(12) United States Patent
Zietsma

(10) Patent No.: US 9,005,133 B2
(45) Date of Patent: Apr. 14, 2015

(54) APPARATUS FOR USE IN DIAGNOSING AND/OR TREATING NEUROLOGICAL DISORDER

(75) Inventor: Rutger Christiaan Zietsma, Tyne & Wear (GB)

(73) Assignee: Rutger Christiaan Zietsma, Tyne & Wear (GB)

( * ) Notice: Subject to any disclaimer, the term of this patent is extended or adjusted under 35 U.S.C. 154(b) by 14 days.

(21) Appl. No.: 13/697,754

(22) PCT Filed: May 11, 2011

(86) PCT No.: PCT/GB2011/050898
§ 371 (c)(1),
(2), (4) Date: Nov. 13, 2012

(87) PCT Pub. No.: WO2011/141734
PCT Pub. Date: Nov. 17, 2011

(65) Prior Publication Data
US 2013/0060124 A1 Mar. 7, 2013

(30) Foreign Application Priority Data
May 14, 2010 (GB) .................................. 1008089.3

(51) Int. Cl.
*A61B 5/00* (2006.01)
*A61B 5/11* (2006.01)
*A61B 5/22* (2006.01)
(Continued)

(52) U.S. Cl.
CPC .............. *A61B 5/4082* (2013.01); *A61B 5/1101* (2013.01); *A61B 5/225* (2013.01); *G06F 3/03545* (2013.01); *G06F 3/041* (2013.01); *A61B 5/1124* (2013.01); *A61B 5/6825* (2013.01); *A61B 5/726* (2013.01); *A61B 2562/0219* (2013.01); *G06F 2203/0384* (2013.01);
(Continued)

(58) Field of Classification Search
CPC ............... A61B 2560/0418; A61B 2560/0425; A61B 2562/0219; A61B 5/1101; A61B 5/1124; A61B 2503/08; A61B 2505/07
USPC ...................... 60/407–480; 600/407–480, 552
See application file for complete search history.

(56) References Cited

U.S. PATENT DOCUMENTS 4,874,053 A * 10/1989 Kimura et al. ................. 180/443

FOREIGN PATENT DOCUMENTS

DE 102005017936 A1 10/2006

OTHER PUBLICATIONS

PCT International Search Report and Written Opinion, PCT/GB2011/050898, Aug. 8, 2011.
(Continued)

*Primary Examiner* — Sanjay Cattungal
(74) *Attorney, Agent, or Firm* — Quarles & Brady LLP

(57) ABSTRACT

An apparatus (2) for use in diagnosing and/or treating a neurological disorder is disclosed. The apparatus comprises a sensor device (4) designed to resemble a pen to provide a first signal containing first data representing a force applied by at least one finger of the subject, an integrated writable surface (10) to (i) provide at least one second signal containing second data representing a position of the sensor device (4) relative to the writable surface (10) and/or (ii) provide at least one third signal containing third data representing an engaging force of the sensor device on the writable surface, and a camera (20) to provide at least one fourth signal containing fourth data representing a position of at least one part of an arm of the subject holding the sensor device (4).

8 Claims, 11 Drawing Sheets

(51) Int. Cl.
*G06F 3/0354* (2013.01)
*G06F 3/041* (2006.01)

(52) U.S. Cl.
CPC *A61B 2560/0418* (2013.01); *A61B 2560/0462* (2013.01); *A61B 2560/0487* (2013.01); *A61B 2562/04* (2013.01)

(56) References Cited

OTHER PUBLICATIONS

Aly, et al., A Novel Computer-Based Technique for the Assessment of Tremor in Parkinson's Disease, Age and Ageing, 2007, 36:395-399.

Dose, et al., Towards an Automated Analysis of Neuroleptics' Impact on Human Hand Motor Skills, Proceedings of the 2007 IEEE Symposium on Computational Intelligence in Bioinformatics and Computational Biology, pp. 494-501.

Hook, et al., A Novel Digitizing Pen for the Analysis of Pen Pressure and Inclination in Handwriting Biometrics, D. Maltoni and A.K. Jain (Eds.): BioAW 2004, LNCS 3087, pp. 283-294.

Unlu, et al., Handwriting Analysis for Diagnosis and Prognosis of Parkinson's Disease, N. Maglaveras et al. (Eds.): ISBMDA 2006, LNBI 4345, pp. 441-450.

* cited by examiner

FIG. 1
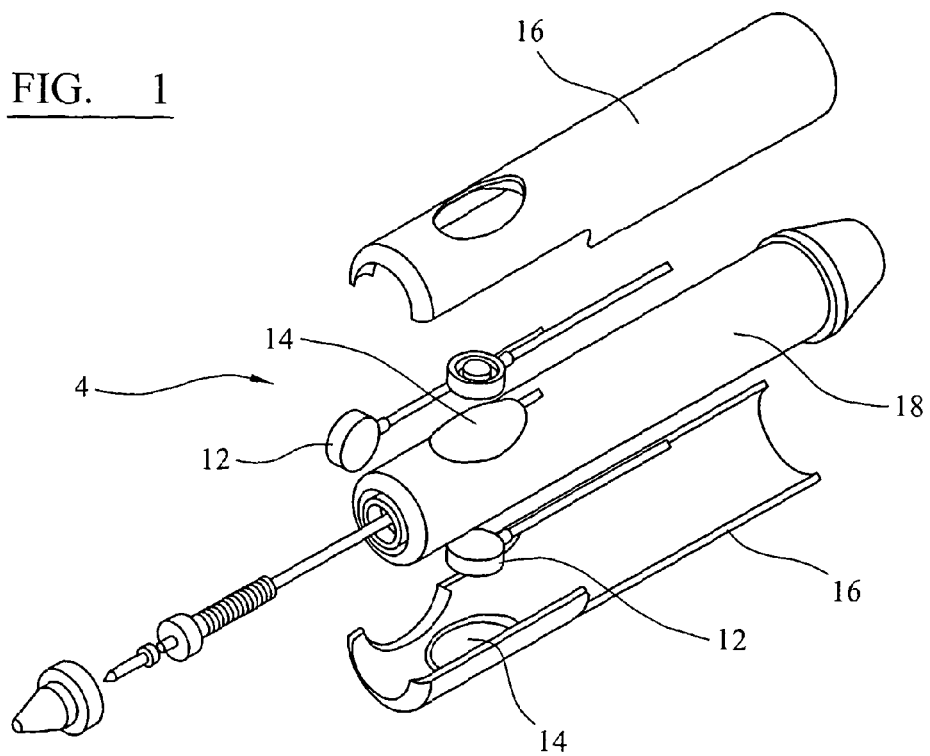
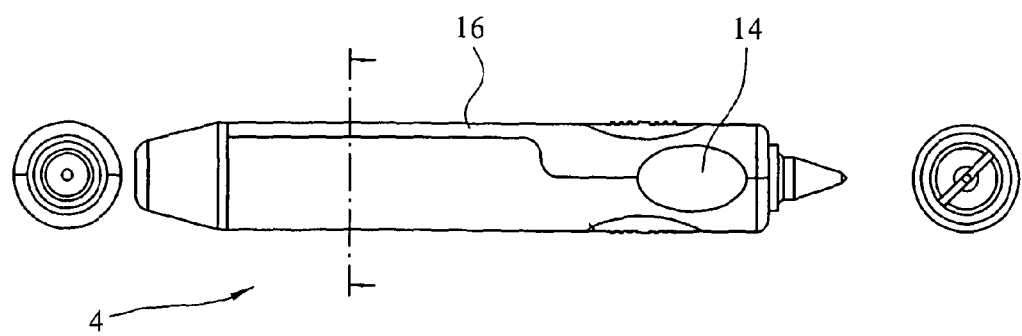
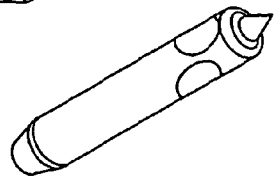
FIG. 2

APPARATUS FOR USE IN DIAGNOSING AND/OR TREATING NEUROLOGICAL DISORDER

CROSS-REFERENCE TO RELATED APPLICATIONS

This application represents the national stage entry of PCT International Application No. PCT/GB2011/050898 filed on May 11, 2011 and claims the benefit of Great Britain Patent Application No. 1008089.3 filed May 14, 2010. The contents of both of these applications are hereby incorporated by reference as if set forth in their entirety herein.

The present invention relates to an apparatus for use in assessment of the human neuromuscular system, i.e. the processes that the nervous system uses to control muscle motion, and specifically diagnosing at least one neurological disorder or other types of disorders, e.g. originating from a mechanical motion constraint (e.g. arthritis), and relates particularly, but not exclusively, to an apparatus for use in diagnosing Parkinson's disease.

Parkinsonism is primarily a disease of the elderly and middle-aged, but can occur in all age groups. Unfortunately, signs of Parkinson's disease (PD) are often still wrongly diagnosed by ascribing the signs of the disability to normal aging. Particularly younger people who have developed a mild initial form of the disease are often wrongly diagnosed as there currently are no appropriate diagnostic methods or products available to clinicians.

A patient can be diagnosed as having a Parkinsonian syndrome or Parkinsonism, if two out of three cardinal signs are seen. These signs are: 1) rigidity (muscular stiffness throughout the range of passive movement in a limb segment); 2) bradykinesia/akinesia (slow/no movement execution), which is most disabling and 3) tremor (postural/during activity). Not all Parkinsonism originates from idiopathic Parkinson's disease with an underlying dopamine defect, but could be caused by other pathologies, such as PSP (Progressive Supranuclear Palsy), MSA (Multi System Atrophy) and rarer CBGD (Cortico Basal Ganglionic Degeneration).

Current diagnostic methods are based on the clinician's subjective interpretation of the patient's performance of writing, spiral drawing and daily living tasks, such as holding a cup, but this interpretation is not objective. Therefore, no reliable comparison can be made from interpretations of samples that were taken at different moments. In addition, the three prominent signs can often not be seen in early Parkinsonism, but 7-10 years before obvious manifestation of the disease, pre-diagnosis neurodegeneration has often already set in. Because of this, diagnosis is not possible until the disease has advanced to a highly significant degree; typically, severe irreversible 60% degeneration of the nigrostriatal neurons has already taken place, resulting in severe deterioration of motor function and development of non-motor symptoms. The key to early diagnosis, leading to early intervention and an improved overall outcome for the patient lies in measuring and quantifying the earliest changes in the neuromuscular system due to Parkinsonism.

Early diagnosis of Parkinsonism becomes particularly useful with the development of neuroprotective therapy and regeneration. Currently, medication and training allows the symptoms of PD to be suppressed, but unfortunately, no cure exists today. However, treatments that enable neuroprotection and regeneration are likely to become available in the near future.

Currently, 0.5% of people over 60 years of age and 2% of people over 80 years suffer from PD. There currently are less than 400 neurologists in the UK and the ratio of neurologists to patients is currently 1:177,000, compared with 1:26,000 (US) and 1:8,000 (IT). Consequently, patients often do not get the required care, and it can be concluded that it is highly important that the neurologist's time be spent efficiently.

In addition, it has been recognised that PD patients are often still wrongly diagnosed. Diagnostic error rates of 47% and 26% have been found. A lower error rate has been reported in standard neurologic and geriatric practice and special movement disorder clinics. This indicates that expert knowledge of movement disorders enables a more accurate differential diagnosis, which is supported by the fact that the diagnostic error rate appears lower in other parts of the world, where more clinicians are available. In 2008 it was found from a study in 10 European sites that PD is still commonly over-diagnosed in Europe.

JP 2000023985 discloses an apparatus for simplifying electromyography for disease of the central nervous system comprising a tablet and a pen with pressure sensors. The finger tip pressures and pen position during movement are stored and analysed by the computer. However, the arrangement of JP 2000023985 does not record all possible measures of handwriting, as a result of which the diagnosis which can be achieved is of limited accuracy.

Preferred embodiments of the present invention seek to overcome one or more of the above disadvantages of the prior art.

According to the present invention, there is provided an apparatus for use in diagnosing and/or treating at least one neurological disorder in a subject, the apparatus comprising:

(a) first detector means adapted to be held by a hand of the subject and to provide at least one first signal containing first data representing a respective force applied to said first detector means by at least one finger of the subject;

(b) second detector means adapted to be engaged by said first detector means when held by the subject, wherein said first and/or said second detector means is adapted to (i) provide at least one second signal containing second data representing a position of said first detector means relative to said second detector means and/or (ii) provide at least one third signal containing third data representing an engaging force of said first detector means on said second detector means;

(c) third detector means adapted to provide at least one fourth signal containing fourth data representing a position of at least one part of an arm of the subject holding the first detector means; and (d) processor means for processing (i) said first data, (ii) said second data and/or said third data, and (iii) said fourth data to determine potential presence of at least one neurological disorder in the subject.

By providing third detector means adapted to provide at least one fourth signal containing fourth data representing a position of at least one part of an arm of the subject holding the first detector means, this provides the advantage of providing a more accurate diagnosis of neurological disorders such as Parkinson's disease.

Said first detector means may comprise at least one first force transducer for providing at least one respective said first signal.

Said first detector means may comprise at least one second force transducer for providing at least one respective said third signal.

The second detector means may have an engagement area having at least one position detector for providing at least one said second signal.

The third detector means may comprise at least one camera.

The processor means may be adapted to compare (i) said first data, (ii) said second data and/or said third data, and (iii) said fourth data with stored values.

This provides the advantage of enabling the data values to be compared with data values for typical healthy subjects and/or subjects suffering from one or more neurological disorders.

The apparatus may further comprise fourth detector means for providing at least one fifth signal containing fifth data representing an orientation of said first detector means.

The processor means may be adapted to determine frequency components and/or phase of said first and/or second and/or third and/or fourth data.

This provides the advantage of enabling accurate differentiation between different forms of neurological disorder, in addition to enabling feedback to be provided to the patient for training/rehabilitation purposes.

The apparatus may be adapted to display a trace to be followed by the subject using said first detector means.

The processor means may be adapted to determine a probability of presence of at least one said neurological disorder.

This provides the advantage of enabling specialist medical resources to be concentrated on further investigation in cases where said probability is high.

A preferred embodiment of the invention will now be described, by way of example only and not in any limitative sense, with reference to the accompanying drawings, in which:

FIG. 1 is an exploded perspective view of a writing device of an apparatus embodying the present invention;

FIG. 2 is a side view of the writing device of FIG. 1;

BACKGROUND

Figure 3:
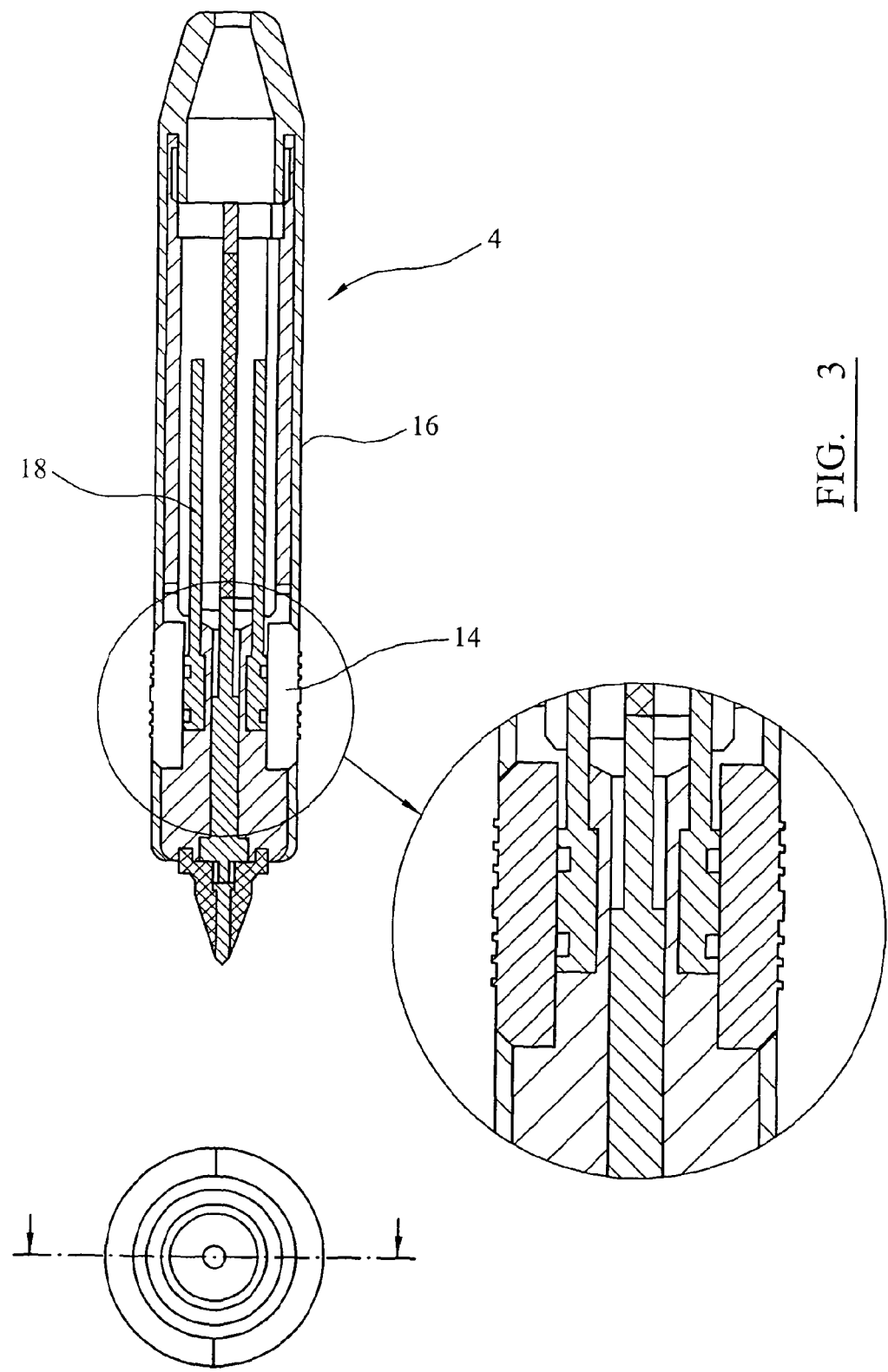
FIG. 3 is a schematic side cross-sectional view of the writing device of FIG. 1.
Figure 4:
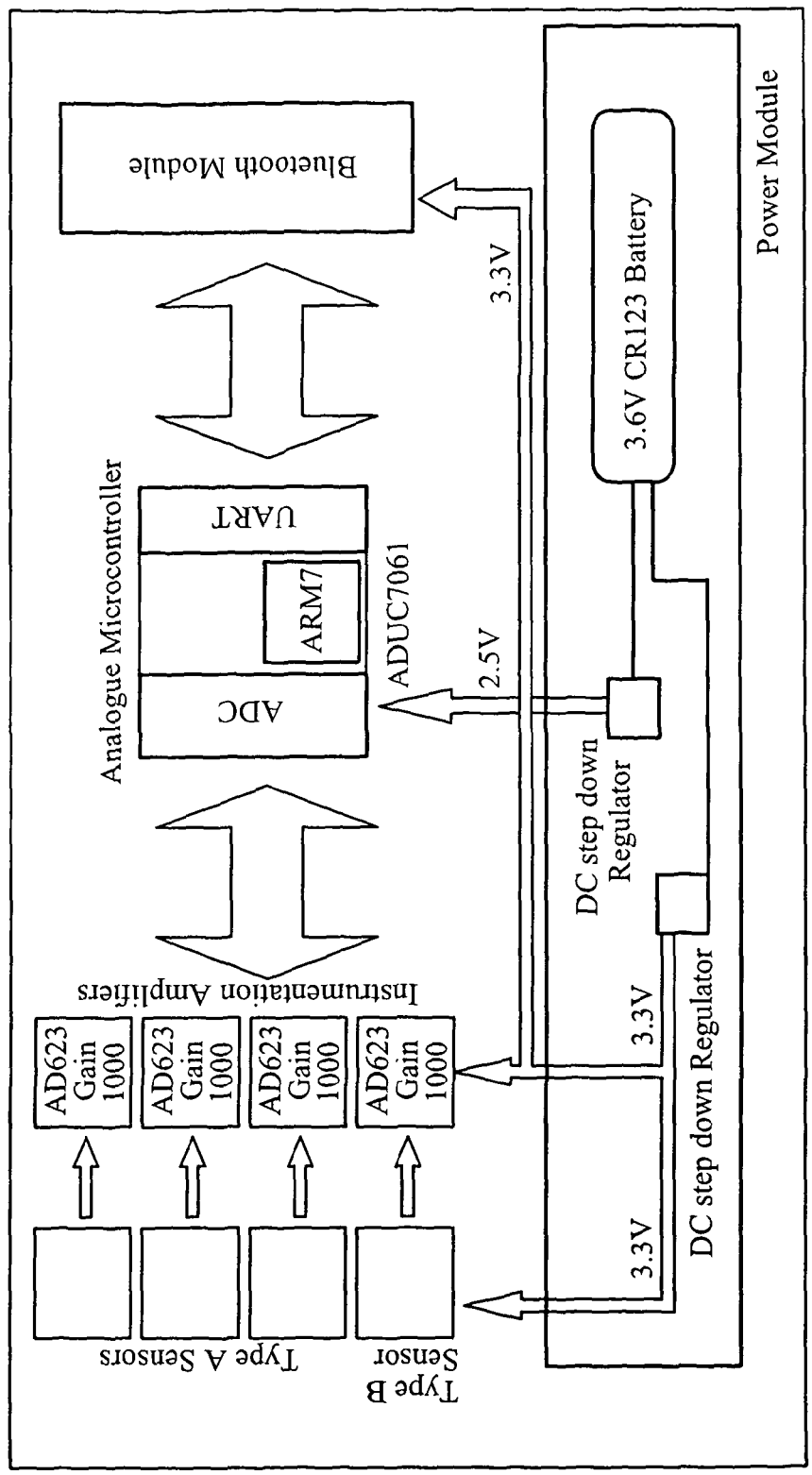
FIG. 4 is a block diagram of the control electronics of an apparatus embodying the present invention.

Diagnostic Concept I: Finger Coordination Discriminates Healthy vs. PD

Many years before Parkinsonism is diagnosed, the handwriting of premorbid patients already presents some specific spatial features, such as less round strokes and more abrupt changes of direction. Studies have reported about handwriting changes due to aging and Parkinson's disease. These changes can be observed from inspecting the patients' handwriting. Research on precision grip in Parkinsonism shows several general impairments in function, including a slowing of the pre-loading phase and a stepwise development of grip force. It has also been reported that Parkinsonism patients tend to produce excessive forces in both static and peak force application.

Research on how the neuromotor system makes decisions that enable handwriting to be accurately performed describes the importance of 'finger synergies' in pen-hand coordination. The finger synergies are defined as the controlled covariation of finger forces and the theory describes how the fingers work together to produce the planned movement. This concept refers to the organization of movement execution by making use of controlling both 'pen grip forces' and 'pen grip moments' that are applied by the fingers to a pen. It is also known for picking up and holding objects in healthy subjects that the forces applied to the object by the fingers are controlled in an organised fashion by the nervous system, where all fingers work together. It is anticipated that any impairment to the writing ability due to Parkinsonism will lead to a specific loss of such normal finger synergies, which can be measured as pen grip force. This has been tested for lifting and holding of different types of objects other than a pen. Changes in patterns of grip force and other characteristics, such as force amplitude and frequency of grip force modulation were observed. PD patients will show specific changes of finger synergies.

Although initially only rest tremor was described in Parkinsonism, today it is generally accepted that Parkinsonism can also be accompanied with kinetic tremor. From frequency analysis of grip force application, differences have been observed between PD patients and a control group, especially in PD patients exhibiting obvious action tremor (AT) at a single modal frequency. These subjects have shown a systematic disruption from force synchronisation patterns that are normally observed between digits, a shift of phase-differences away from ~0° (in-phase), which typically occurred at and around the AT frequency, while at many other frequencies synchronisation patterns were still maintained. As the disruption is very specific and focal and patients make no quantifiable attempt to compensate for the lack of force synchronisation at AT frequencies, e.g. by increasing total force output, it was believed that this lack of force synchronisation at the digits does not contribute to the lack of manual dexterity often observed in PD patients. This has given rise to the idea that changes in finger synergies, related to planning and coordination of the motion, occur before impairment of function develops.

In the past the use of spiral drawing for diagnostics in PD was common practice. There currently is a renewed interest in opportunities for spiral drawing and computerized assessment of kinetic tremor. At present the kinetic tremor in patients is hardly examined during clinical practice and no attention is paid to it in clinical rating scales.

Although AT may often be obvious to clinicians, minor tremors and other less obvious changes in the frequency domain of grip force application may not be. The grip force modulation frequencies will be different in PD/Parkinsonism. An alteration in the time-dependent structure of the signal has also been reported and this is referred to as a change in the regularity of physiological output. Regularity can be quantified by an analysis method in the time domain, referred to as approximate entropy (ApEn). Research has reported that the time-dependent structure of tremor (ApEn) provides valuable additional information beyond that of amplitude and modal frequency analyses and is useful in differentiating tremor in healthy people from those with PD/Parkinsonism.

Diagnostic Concept II: Analysing Limb Tremor for Differential Diagnosis

Including tremor frequency measures adds valuable information to the assessment. PD/Parkinonism patients typically show low frequency tremor between 3-8 Hz and more frequently the range is 3-5 Hz (Table 1). Parkinson's disease is often confused with Essential Tremor (ET). ET affects 2-3% of the population and is more benign than PD. ET patients typically show tremor in the range 4-12 Hz (Table 1). Healthy subjects may show physiological tremor, which is the oscillation of a body part resulting from the interaction of normal mechanical reflex mechanisms and a central oscillator. The frequency is usually between 8 to 12 Hz, but frequencies up to 25 Hz have been observed. It can be concluded that tremor between 3-8 Hz in addition to other clinical manifestations points towards PD/Parkinsonism.

TABLE 1

Tremor differentiation based on origination and showing the frequency band.
Properties of several basic tremor types

| Tremor type | Frequency | Activation condition | | |
|---|---|---|---|---|
| | | Resting | Postural | Kinetic |
| Parkinsonian | 3-7 Hz | X | x | x |
| Essential | 4-12 Hz | | X | x |
| Physiological | 3-30 Hz | | X | |
| Enhanced physiological | 8-12 Hz | | X | |
| Dystonic | 4-7 Hz | | X | X |
| Task-specific | 5-7 Hz | | | X |

X - characteristic condition;
x - occurs in some

Figure 7:
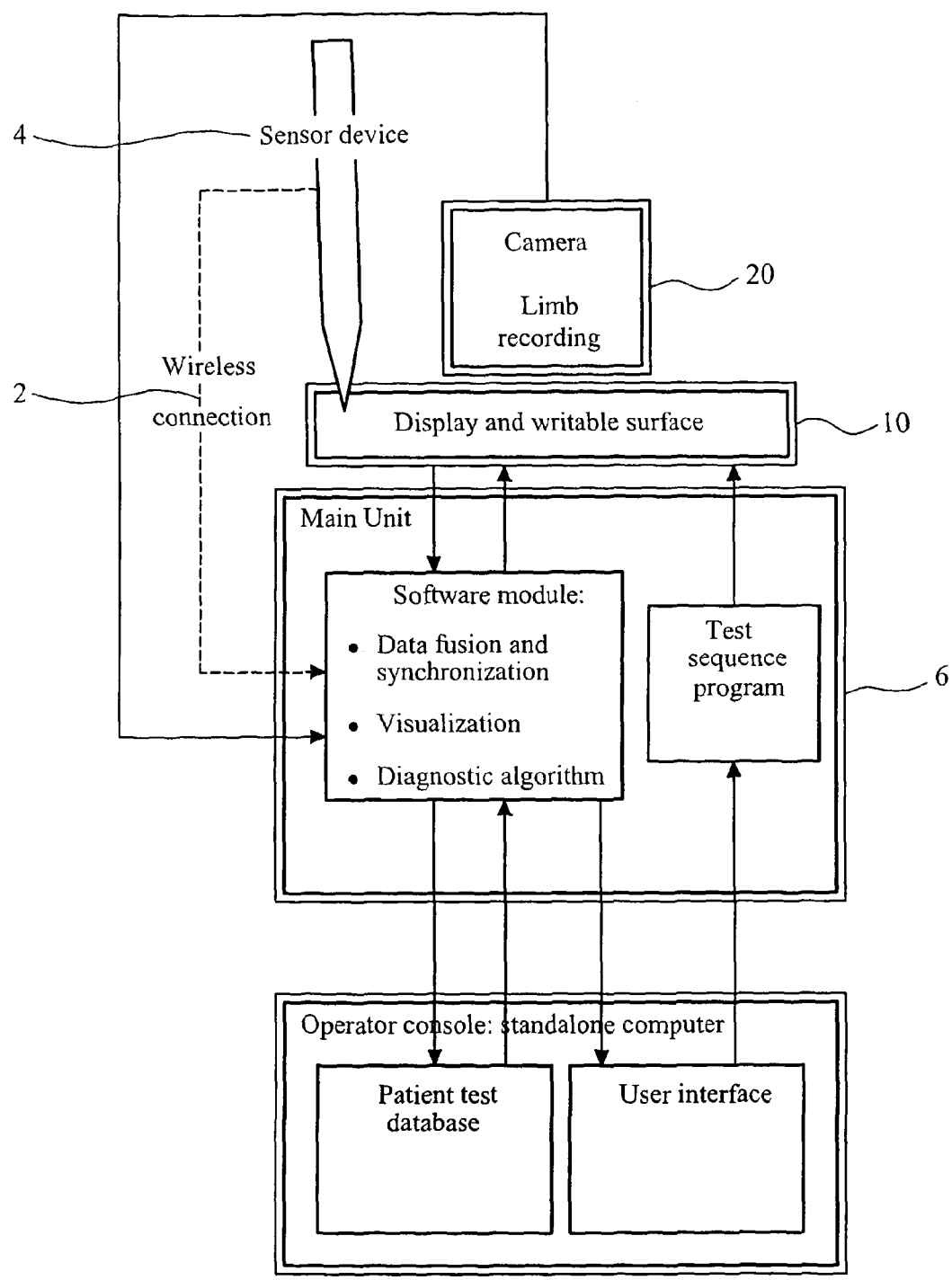
FIG. 7 is a schematic system overview of an apparatus embodying the present invention.
Figure 8:
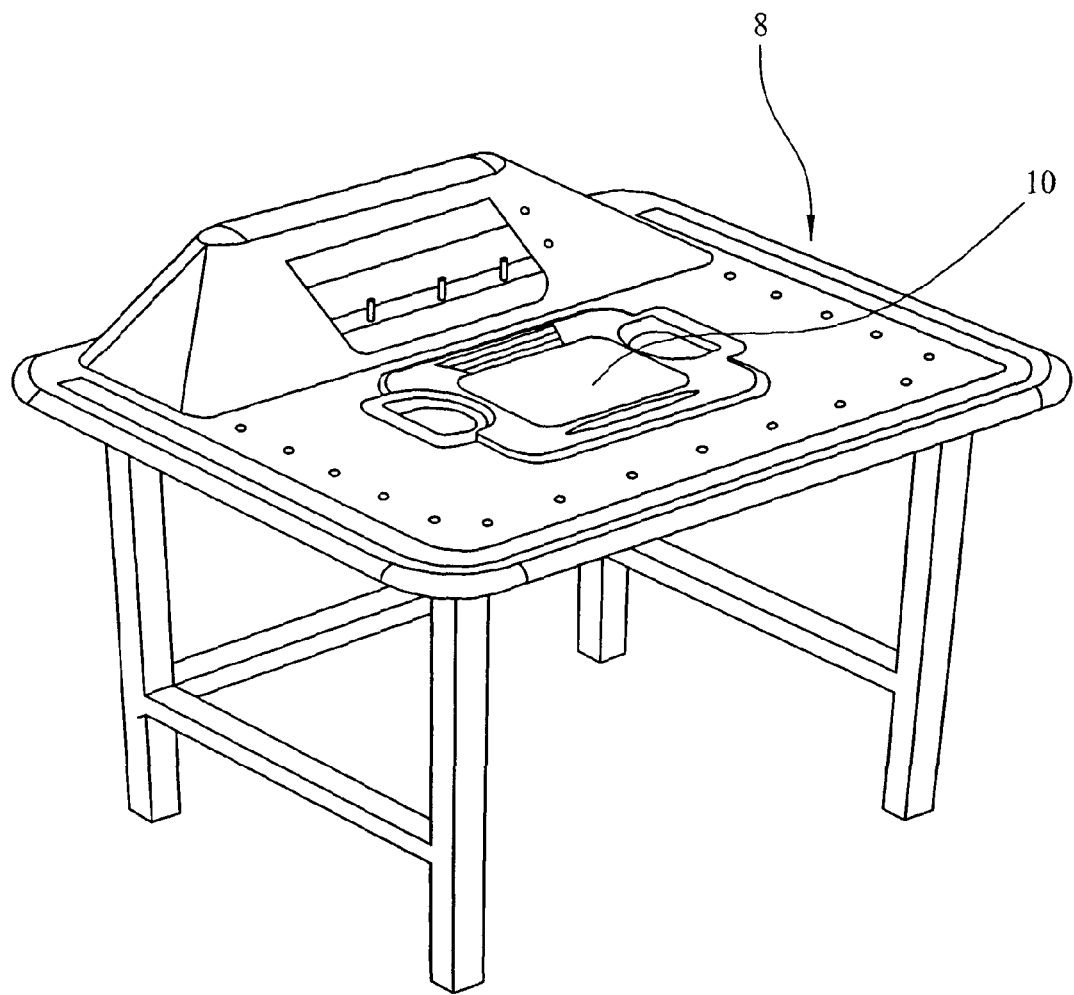
FIG. 8 is a perspective view of a writing table having a writing tablet forming part of the apparatus of FIG. 6.

Referring to FIG. 1, a diagnostic system 2 embodying the present invention is shown in overview FIG. 7 and comprises a sensor device 4 (shown in more detail in FIGS. 1 and 2) designed to resemble a pen, and a main unit 6 in the form of a standalone computerized hardware device, using embedded system technology for synchronising and fusing of data, data processing and storage and incorporating a test sequence program, and built into an ergonomically designed table 8 (FIG. 8) with integrated writable surface 10 that records and displays drawing and script during patient assessment, e.g. by means of touch sensors on a display. The main unit is also provided with digital cameras 20 (FIG. 8, 9) for recording pen, hand and limb joint motion, e.g. implementing a stereoscopic system with two identical cameras 20 separated by a known short distance that both face the tablet device (FIGS. 7 and 8) or alternatively an inertia sensor system could be implemented on the subject's upper limb.

Figure 5:
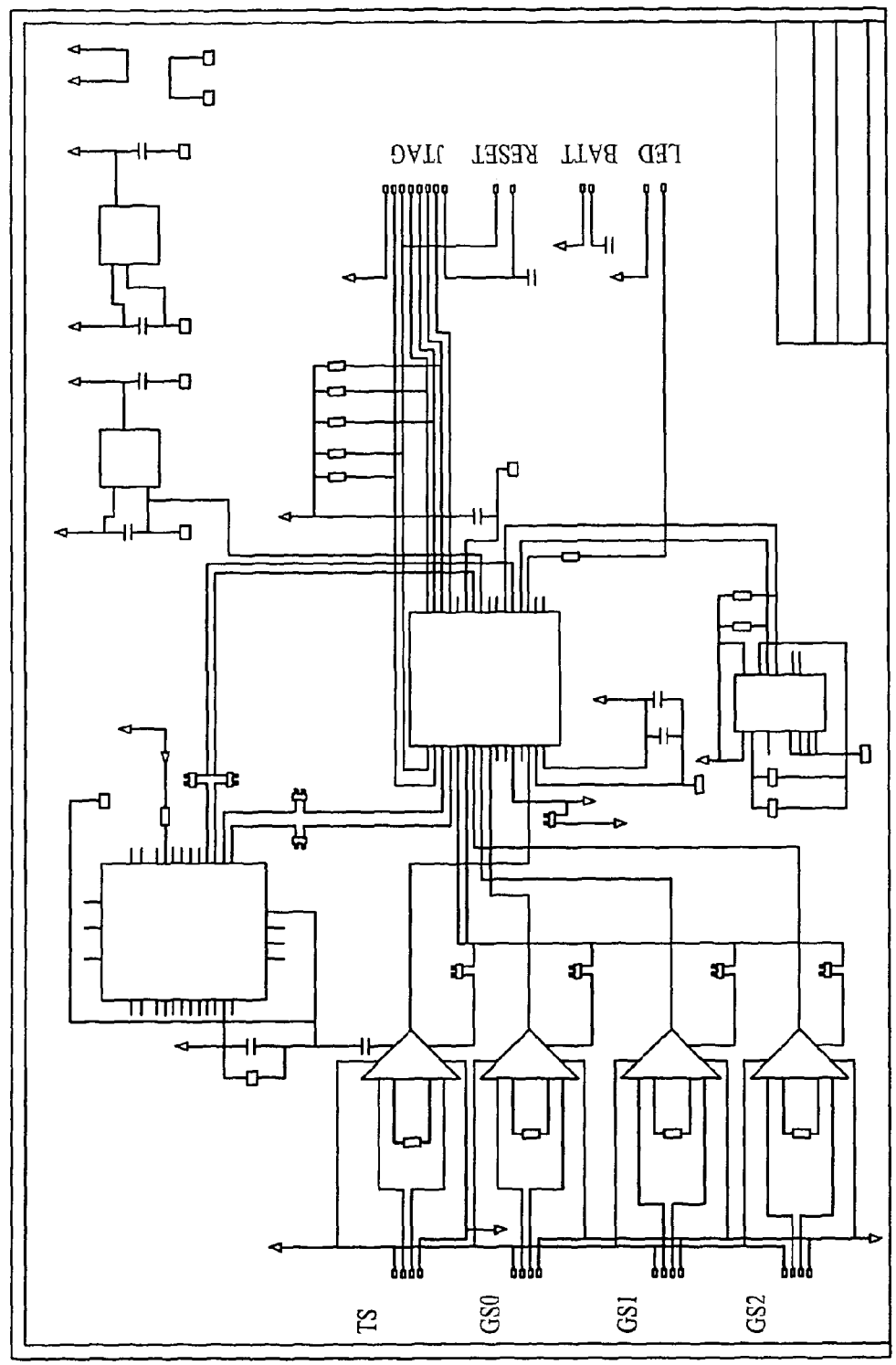
FIG. 5 is a schematic diagram of electronic circuitry of the writing device of FIG. 1.
Figure 6:
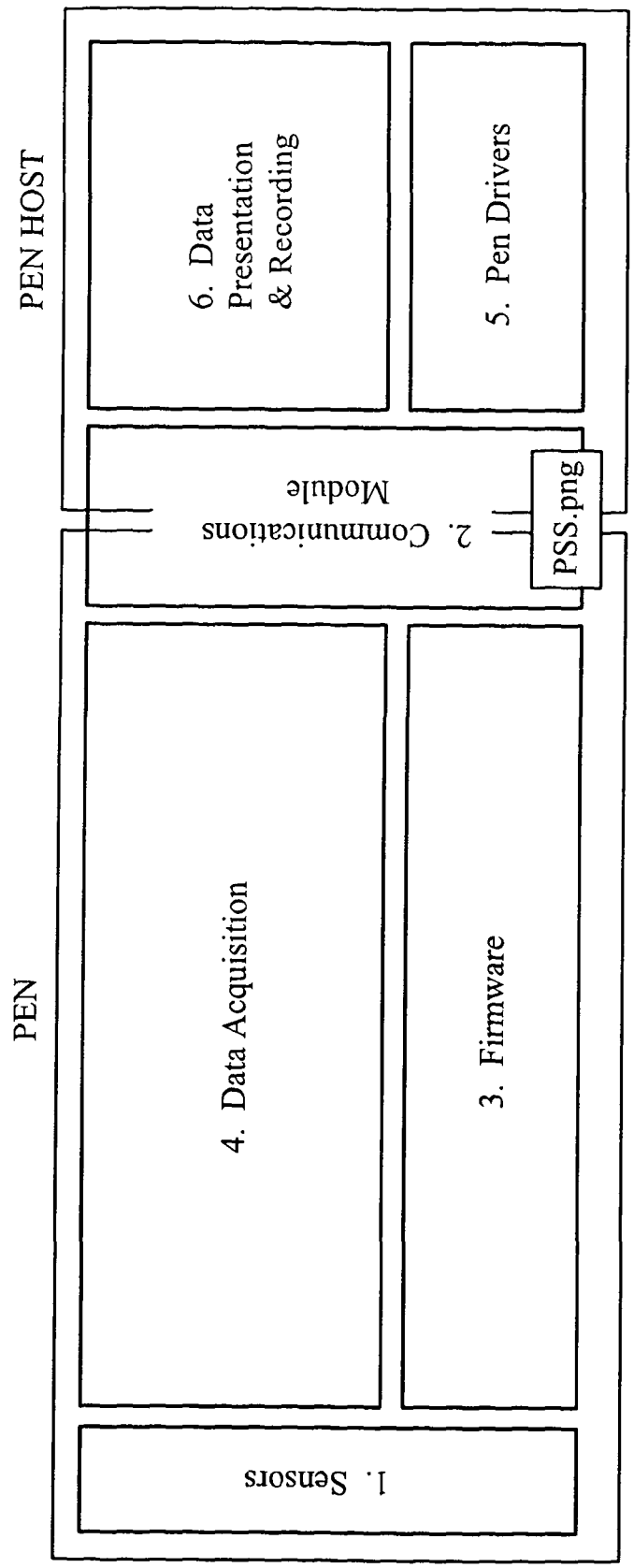
FIG. 6 is a block diagram of the pen-like sensor device sub-systems within the main unit.

The sensor device 4 looks and feels like an ordinary pen, but measures pen grip forces applied by the thumb, index and middle finger as well as linear and angular velocity and acceleration from which the pen orientation can be determined. The sensor device 4 contains finger force sensors 12 that measure the force applied by thumb, index and middle finger, which are mounted between respective pressure pads 14 in recesses in body clamshells 16 and an internal body 18. In addition, internally the sensor device 4 incorporates a combination of 3-axes gyroscopes and 3-axes accelerometers to record pen angular velocity and linear acceleration, respectively over time. The sensor device 4 contains an electronic printed circuit board (FIG. 5) and firm ware for signal conditioning, basic processing, an analogue to digital conversion module and a communication module for transmitting the data through a wireless connection to the main unit 6 (FIGS. 6 and 7). The Pen Host on the main unit contains drivers to interface with the pen and enable recording and visualising of the data.

The sequence of pen tip coordinate data that is recorded from the writable surface 10 is continuously transmitted through a wired connection to the main unit. The camera data is also transmitted to the computer of the main unit via a cable.

The force and inertia sensors 12 within the sensor device 4 measure the pen grip force applied by the fingers, the pen tip pressure applied to tip 22 and pen motion/acceleration, which reveals how the sensor device 4 and hand interact. Signal processing techniques allow extraction of information from the grip force and motion signals about the functioning of the neuromuscular system. Importantly, subtle changes from the 'normal' neuromuscular activities (observed in healthy subjects) that are specifically associated with early PD can be detected with the proposed system by means of assessing the combined measures. This is further explained below: the principal changes of neuromuscular activities associated with PD patients and basic principles of the novel diagnostic system that record these activities.

During patient screening with the apparatus 2, the patient is asked to perform a set of writing and/or drawing activities, which will typically take 20 minutes, which includes the set up time. The following biomechanical parameters are recorded:

Force applied by the thumb, index and middle finger to the sensor device 4, revealing the finger muscle motion/coordination;

Pen tip pressure;

Pen, finger, hand and arm joint motion;

Resulting script.

Example Case

A 65 year old patient is referred by a GP to a neurologist. There is tremor in the person's right hand both during rest and during action (e.g. controlling cutlery during eating). The tremor was first noticed 18 months ago, but due to waiting lists to see a neurologist, it has not been possible to diagnose the patient and give any treatment. The patient also exhibits the following other symptoms: limb stiffness (rigidity) and slowness of motion (akinesia/bradykinesia). No psychological or mental deterioration can be seen at first sight. The GP, who referred the patient believes the patient has PD.

The Problem

One of the difficulties with diagnosing Parkinson's diseases in the early stages is that it can be mimicked by other more benign conditions, particularly essential tremor (ET). Many people with ET worry that they have Parkinson's disease and this causes a lot of concerns for patients and their GPs and generates a lot of work for neurology departments sorting the two out.

Differentiating between Parkinsonism and ET can be difficult even for experienced physicians. Both history and the triad of Parkinsonism's physical symptoms are taken into account to distinguish between ET and PD. Particularly identifying different types of rest tremor takes an important place. ET patients usually have had tremor for a long time. PD patients on the other hand tend to contact a primary care physician within 6 months from development of the first symptoms. If a rest tremor is observed from the hands while the hands rest in the lap or while subjects walk with their hand by their sides, this may point towards PD. In essential tremor typically a symmetrical postural tremor is observed in patients both during rest and action, whereas PD patients usually exhibit an asymmetrical rest tremor, which disappears when a posture is maintained. To conclude, PD normally presents itself as a resting tremor whilst ET is an action tremor that worsens with movement. However, occasionally Parkinsonism is accompanied with an action tremor and ET may have other symptoms that resemble Parkinsonism.

The case described above is confusing for clinicians as both rest and action tremor are observed, which points towards ET, but other symptoms that resemble PD are also seen. In this case, consultant neurologists will struggle to make the correct diagnosis. Consultant neurologists specialised in movement disorders will still misdiagnose in 5% of the cases. All other healthcare workers, who are less experienced, will not be able to make the correct diagnosis. As the availability of consultant neurologists is poor in the UK (400 nationwide), it is estimated that misdiagnosis occurs in 50% of the cases by those clinicians who are less experienced.

Using the Apparatus

During patient screening with the apparatus 2, the patient is asked to perform a set of writing and/or drawing activities that may include all or some of the following:

(i) Hold the sensor device 4 without performing any writing task and without keeping a fixed posture for assessing rest tremor while tremor is not suppressed.

(ii) Line drawing from point A to point B with the pen over the drawing surface of the table, following a fixed line or moving point that is displayed on the writing surface, to assess akinesia/bradykinesia and motor blocks.

(iii) Spiral drawing (free drawing or tracing) to assess action tremor and to localise the tremor origin.

In addition, other movements that are not related to handwriting will be examined:

(iv) Continued finger tapping;

(v) Continued pro-/supination movement of hands;

(vi) Continued opening and closing of arms.

The following parameters are measured and analysed from recordings (i) to (vi):

1) Light Pen Rip during Rest:

Rest tremor is measured from the finger (grip) forces and frequency analyses. This method reveals rest tremor only. A patient may be asked to simultaneously perform another task, e.g. talk while holding the sensor device 4 as this will ensure that the patient is not suppressing tremor. The tremor measured from the finger forces includes both distal tremor that originates from the fingers and proximal tremor that originate from the rest of the limb. With other impairments than PD, the tremor frequency is related to the origin of the tremor. With PD the tremor origin cannot be localised. A database with profiles of healthy subjects and impaired subjects is used as a reference.

2) Line Drawing:

a. Assess if any delays/inability (radykinesia/akinesia) to initiate motion occur or if any motor blocks occur while performing motion. This is analysed from the timing of finger force and limb motion activities. A database with profiles of healthy subjects and impaired subjects will be used as a reference.

b. The finger coordination and underlying neuromuscular processing is assessed from finger grip force measurement and analysis that reveal how the fingers work together to enable the pen to establish pen motion. The system will provide an output of whether the 'finger synergies' are healthy or impaired. A database with profiles of healthy subjects and impaired subjects is used as a reference.

c. Rigidity is assessed from analysis of muscle activity that is measured from the finger grip forces and limb motion. A database with profiles of healthy subjects and impaired subjects is used as a reference.

3) Spiral Drawing:

Tremor is assessed from the tip 22 of the sensor device 4, recordings of joint motion and finger force recordings on the sensor device 4. The tremor analysis includes both distal tremor that originates from the fingers and proximal tremor that originate from the rest of the limb. With other impairments than PD, the tremor frequency is related to the origin of the tremor. With PD, there is no clear localised tremor origin (muscle groups) as the tremor is generated in the central nervous system and different muscle groups can be affected (e.g. neck, arm). A database with profiles of healthy subjects and impaired subjects will be used as a reference.

1) Finger Tapping

Alterations in finger movement patterns are quantified. The sensor device is not required for this test, but the task will be performed in front of the recording table 8. The ability to perform continuous finger tapping is known to deteriorate with Parkinsonism. The changes in timing of the movement and range of motion with each repetition can be quantified. A database with profiles of healthy subjects and impaired subjects is used as a reference.

2) Pro-/Supination Movement of Hands

Alterations in finger movement patterns are quantified. The pen is not required for this test, but the task will be performed in front of the recording table. Alterations in pro- and supination movement patterns are quantified. The ability to perform continuous pro-/supination movement of hands is known to deteriorate with Parkinsonism. The changes in timing of the movement and range of motion with each repetition can be quantified. A database with profiles of healthy subjects and impaired subjects is used as a reference.

3) Opening and Closing of Arms.

Alterations in movement patterns while opening and closing the arms are quantified. Alterations in finger movement patterns are quantified. The sensor device 4 is not required for this test, but the task will be performed in front of the recording table 8. The ability to perform this continuously is known to deteriorate with Parkinsonism. The changes in timing of the movement and range of motion with each repetition can be quantified. A database with profiles of healthy subjects and impaired subjects is used as a reference.

Differentiating Algorithm

Figure 9:
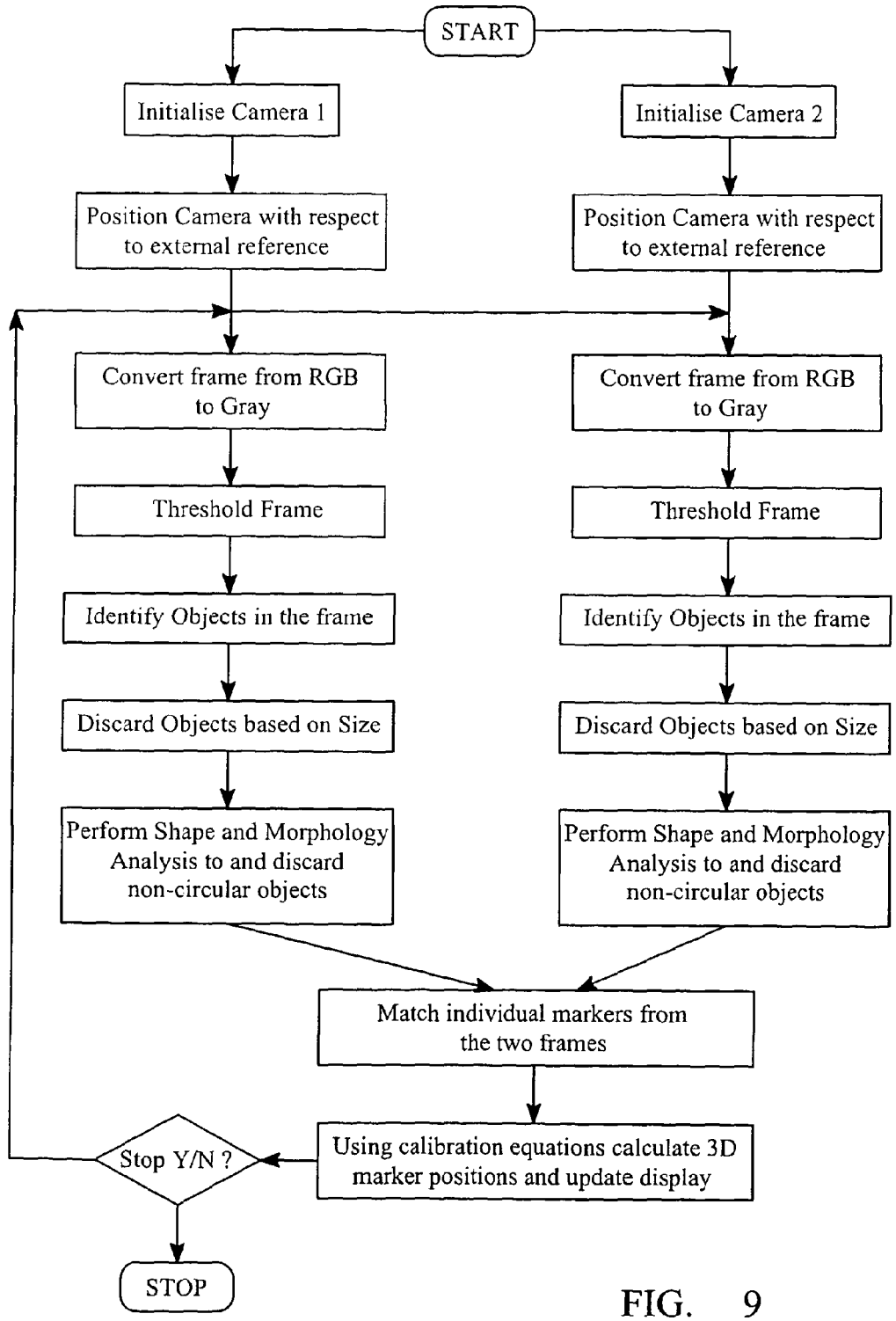
FIG. 9 is a flow chart showing operation of the motion analysis apparatus of FIG. 6.
Figure 10:
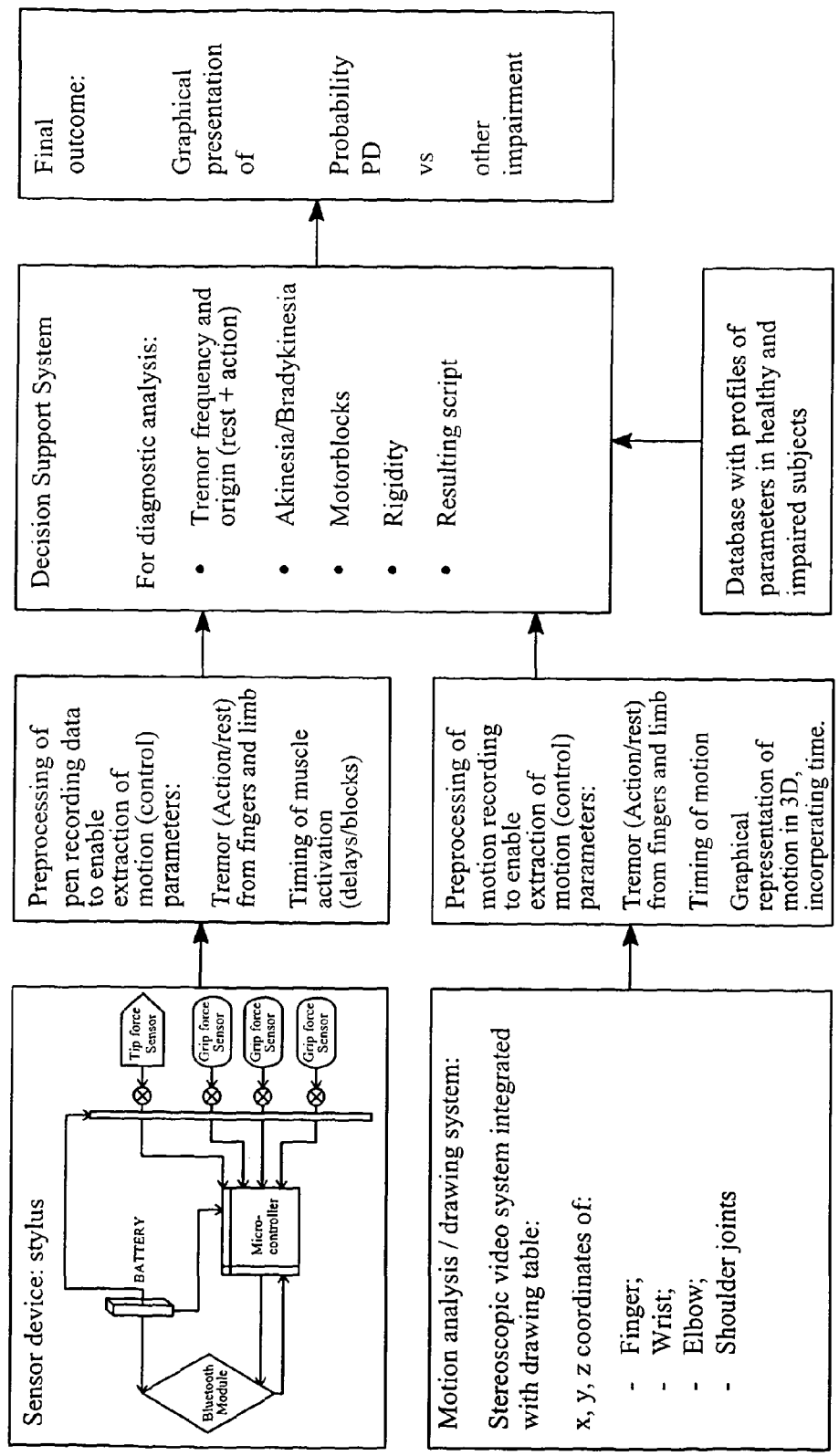
FIG. 10 is a flow chart showing operation of the apparatus of FIG. 6.

All recorded parameters are analysed. The output of various analyses is combined according to the data flow diagram in FIG. 8. The data from both pen grip force measurements and joint recordings is firstly pre-processed, which includes DC term removal, smoothing of data and other filtering techniques dependent on the data quality. This is to ensure that the specific features can be extracted from the data that reveal the neuromotor control behind the execution of the biomechanical motion. A decision support system (DSS), which is detailed in FIG. 9, then analyses the following biomechanical parameters:

Tremor frequency and origin (rest+action)

Finger force coordination

Akinesia/Bradykinesia

Motorblocks

Rigidity

Handwriting: micrographia or otherwise impaired writing

The Decision Support System (FIG. 9) makes decisions based on databases with profiles (known ranges) of biomechanical parameters (joint motion coordinates; finger forces; pen tip force) of healthy subjects, PD patients and patients suffering from other impairments. This knowledge is gained during extensive clinical testing (clinical exploratory testing and clinical trials). The final outcome of the decision support system is a probability that the subject suffers from PD or a number of other impairments (e.g. PD, dystonia, spasticity, ET, psychogenic tremor, enhanced physiological tremor etc). The Decision Support System is explained in more detail below.

The DSS follows the following steps:
1) The following motion control parameters are recorded:
   Joint motion/velocity/acceleration;
   Pen tip motion/velocity/acceleration;
   Thumb, middle and index finger forces;
   Pen tip force.
2) Firstly, all parameters are graphically presented to the operator to obtain immediate feedback from the recording and check for any obvious signs of neuromotor deterioration and whether the test procedure is correctly carried out.
   Secondly, for all parameters an EMD algorithm is executed, which assesses oscillation frequencies of the force and motion signals. Using EMD, any given time series data is firstly composed into a set of simple oscillatory functions by the repeated application of a nonlinear iterative procedure. Then time-dependent amplitudes and frequencies of the simple oscillatory functions are defined using a Hilbert transform. Alternatively, wavelets, which are frequently used in image analysis, could be used to decompose and analyse the grip force and motion patterns. Another useful method is dynamic time warping, which is frequently used to align oscillations of recorded speech when words are spoken with different speed. The technique could also be applied to decompose the grip force patterns. All methods described here will enable the user to obtain frequency content of the recorded control parameters, which when combined will give an output of the presence of action/rest tremor and its frequency.
   Thirdly, for all parameters a pattern recognition algorithm is executed, which analyses for specific motions that have been studied extensively, whether the finger force control and joint motion control follow a normal pattern or if there is impaired function.
3) The above steps described under 2 will for each of the motion control parameters, described under 1, give an indication of the presence of the following markers that reveal the integrity of the neuromuscular system and the presence of impairments:
   Tremor frequency and origin (rest+action)
   Finger force coordination
   Akinesia/bradykinesia
   Motor blocks
   Rigidity
   Handwriting These markers are described in detail below.

Tremor Frequency and Origin (Rest+Action)

Figure 11:
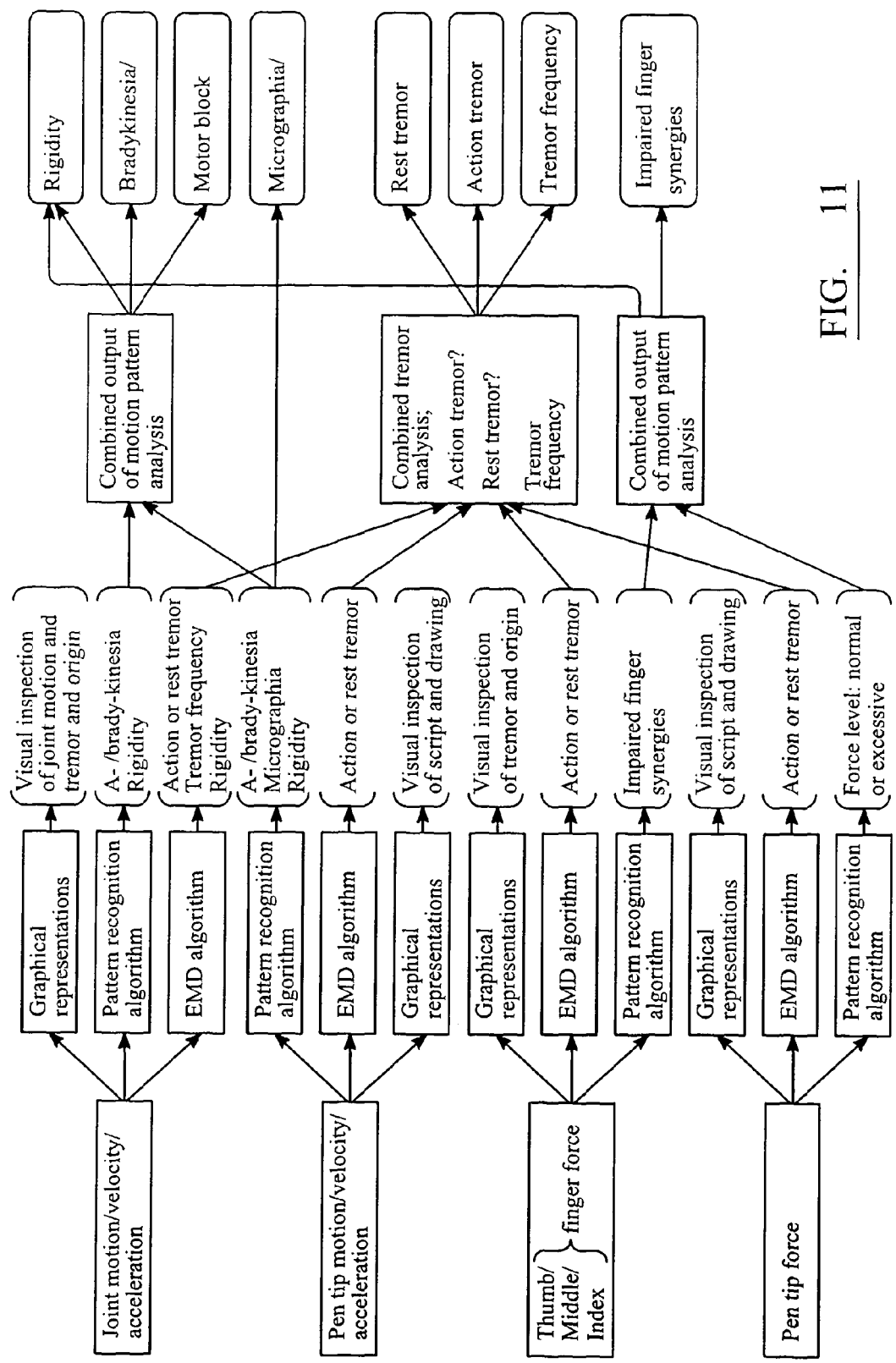
FIG. 11 is a flow chart showing operation of an evaluation algorithm by the apparatus.
Figure 12:
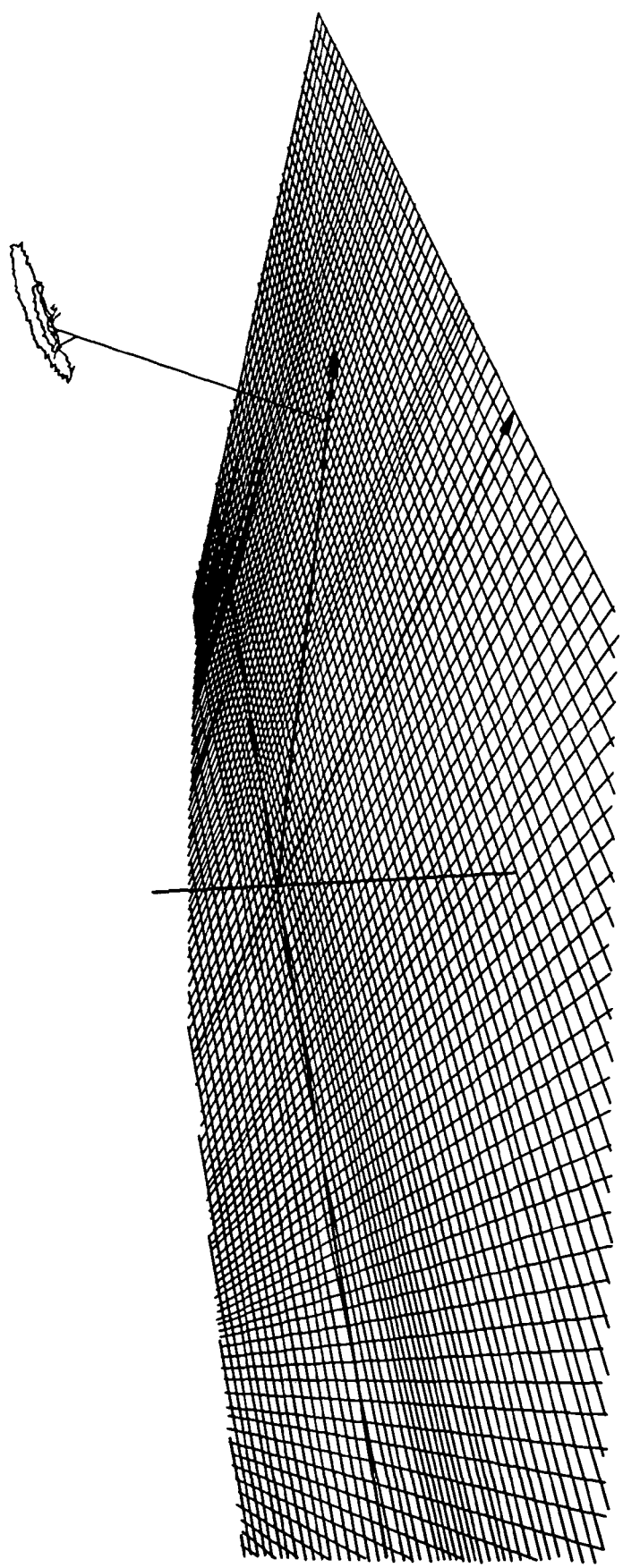
FIG. 12 shows a measurement of pen tip and joint trajectories over time.

Tremor is assessed from both limb joint motion that is recorded with the camera system and from finger force coordination that is measured from the pen grip forces. Both rest tremor and action tremor are analysed. Tremor frequencies measured from the fingers reflect tremor that originates from the limb and hand as well as the fingers. The frequency often relates to the origin, with the lower frequencies corresponding to the limb and hand and higher frequencies originating from the fingers. The joint motion is presented in a 3D graph that includes the timing of the motion and which also reveals the tremor origin (FIG. 11). With PD there is never a clear origin as the tremor originates in the central nervous system due to dopamine defect and the tremor frequency that is induced can occur at different body segments. Tremor is assessed by means of Power Spectral Density analysis of the force and motion recordings. The frequencies relate to different disease profiles according to table 1.

Finger Force Coordination

Finger force coordination is assessed from recordings of finger force application to the sensor device 4. The finger force is typically impaired in PD and reflects the subtle deterioration of neuromotor function due to PD. Therefore, assessing finger coordination enables early neuromotor deterioration to be revealed.

The 'uncontrolled manifold hypothesis', on how the neuromotor system makes decisions that enable handwriting to be accurately performed, describes the importance of 'finger synergies' in pen-hand coordination. The 'uncontrolled manifold hypothesis' is a new phenomenon, which may not be familiar to clinicians skilled in the art of diagnosing motion disorders. The finger synergies are defined as the controlled co-variation of finger forces and the theory describes how the fingers work together to simultaneously control both forces and moments that are applied to a pen to produce the planned movement. This concept refers to the organization of movement execution. It is believed that the present invention would enable the finger synergies as described by this theory to be quantified for the first time: the timing and frequency of force application can be related to the strategy that is adopted by the nervous system to execute the movement.

Finger force coordination is assessed by means of a number of signal processing techniques for feature extraction. These include:
   Force amplitude and derivatives, such as Root Mean Square (RMS) values.
   Power spectral density analysis: one of the main tools used allowing the frequency components of the waveform contained in a physiological signal and the relative power at each frequency to be viewed. Visually this can be easier to follow than structures in the time domain.
   Coherence: Coherence analysis, or cross-spectral analysis, is used to identify signals that have similar spectral properties if the variability of two distinct time series is interrelated in the spectral domain (e.g. high/low power in the same spectral frequency bands).
   Approximate entropy, which gives an average of time series, representing occurrence frequency of similar points. It makes use of the fact that very regular signals of automated movements have a high self-similar degree, whereas signals from PD patients are less similar.
   Multiscale entropy: representing the entropy behaviour due to different time scales.

Akinesia/Bradykinesia

Bradykinesia (slowness of motion) and Akinesia (inability to perform motion) is assessed by looking at the subject's ability to initiate motion from both pen control action, measured from the finger forces onto the sensor device 4 and the motion of limb and finger joints. The drawing table 8 displays a line or alternatively a moving dot or other figure, which the subject attempts to trace. The analyses compare the resulting pen grip action and limb motion and resulting drawing with the drawing that was attempted. The closeness to attempted motion and delays in timing of the motion are quantified on a scale that depends on the time and space that was quantified for the experiment. The results of a number of trials are compared as deterioration with extended motion also indicates neurological problems.

Motor Blocks

Motor blocks, which is a form of akinesia/bradykinesia, can be assessed from line drawing activity in an analogue fashion to assessing akinesia/bradykinesia and will become obvious from line drawing as described for bradykinesia.

Rigidity

Rigidity has recently been successfully assessed by means of Electro Myography (EMG) that records muscle activity. Measuring the muscle activity is also possible from the pen grip forces, which can then be related to stiffness, e.g. using wavelet transforms or other analysis techniques to separate the lead pipe phenomenon and cogwheel phenomenon that can be distinguished in EMG recordings of PD patient to quantify rigidity after determining the optimal filter settings are crucial. A wavelet is a mathematical function used to divide a given continuous-time signal into different scale components. A frequency range can be assigned to each scale component to study them with a resolution that matches their scale. A wavelet transform is the representation of a function by wavelets. Using wavelets to represent the finger forces that result from muscle actions will enable the operator to assess rigidity and compare this with motion (coordinates in 3 dimensions).

Handwriting

Analysing the subject's handwriting is automatsed with a script that assesses the roundness of strokes, size of letters and consistency of writing. Less round strokes and micrography, which is the typical writing of PD patients that is characterised by small letters and often inability of patients to write continuously, can be assessed and stored for monitoring of disease progress and usefulness of treatment.

4) The above markers that reveal the integrity of the neuromuscular system that were obtained from different motion analysis parameters, described under (1), will be combined for the different tests that were carried out. This will lead to a combined conclusion regarding the presence of the markers described under 3 into profiles of:
Motion pattern analysis;
Tremor analysis
Force pattern analysis.

5) Conclusion: Do the motion patterns resemble healthy subjects or patients suffering from PD, dystonia, spasticity, ET, psychogenic tremor, enhanced physiological tremor or other impairments? The conclusion is reported as a percentage of likelihood that the patient suffers from each of these impairments.

Improvement of Diagnostics Healthcare through the Concept

It is envisaged that facilitating each neurology department with the proposed system for fast and reliable diagnosis and disease monitoring could significantly improve the efficiency of patient care in neurology, which will also lead to improved economic efficiency, for the following reasons.

Diagnosis is the key to making an accurate judgement on the most appropriate medical or surgical treatment. Monitoring the disease is required for further management of the disease and re-diagnosis is required with the development of atypical symptoms. A late or wrong diagnosis will certainly lead to a progression of the disease. At that stage secondary complications and extensive costs for daily care, physio- and occupational therapy, treatment with medication and sometimes surgery cannot be avoided any more. Although the current trend for some forms of Parkinsonism is to not immediately start treatment with medication, research results suggest that early diagnosis and treatment is required to improve the patient's health and quality of life. In all cases, early diagnosis will at least enable physical therapy and will lead to better understanding of the disease and response to treatment.

Improving UPDRS

The most widely used standard rating tool to diagnose and follow the longitudinal course of PD is the Unified Parkinson's Disease Rating Scale (UPDRS). However, the UPDRS is not an objective scale for the motor symptoms and is highly inaccurate. UPDRS is made up of 1) mentation, behavior and mood; 2) activities of daily living and 3) motor sections. Normally, a short list of key motor symptoms measures is taken by interview. The key measures include the three cardinal signs (bradykinesia, tremor and rigidity) plus postural instability and gait disorders (PIGD). Quantifiying tremor takes an important place in assessment of motor function as described in the section above titled 'Diagnostic concept II: analysing limb tremor for differential diagnoses. As the UPDRS is currently not an objective scale for the motor symptoms and it is highly inaccurate, the present invention provides an alternative method for performing UPDRS testing with the advantage of electronic data collection. The present invention enables clinicians to objectively assess activities during daily living and motor sections of the UPDRS alongside the UPDRS part 1 (mentation, behavior and mood).

A number of simple quick tests with the system can be defined that are also incorporated with the UPDRS, but with the advantage of objective highly accurate recordings. An important feature is assessing Freezing or motorblock (MB) is the non-volitional sudden discontinuation of motor activity. MB is seen in cued repetitive movements, such as speech, finger tapping, gait, handwriting and point-to-point movements and has been related to UPDRS. It was found that the MB periods could be identified clearly and were related to freezing of hands in motor part UPDRS. For all tested patients, the results were in agreement with the score of clinical rating with UPDRS (Unified Parkinson's Disease Rating Scale), motor part, question nr. 24, part III (≥2 freezing predominant). It is believed that the present invention also enables neurologists to assess repetitive motions, such as handwriting, finger tapping and point to point movement by measuring force application, pen tip and limb joint kinematics and quantify the various phases.

It will be appreciated by persons skilled in the art that the above embodiment has been described by way of example only, and not in any limitative sense, and that various alterations and modifications are possible without departure from the scope of the invention as defined by the appended claims.

The invention claimed is:

1. An apparatus for use in diagnosing at least one neurological disorder in a subject, the apparatus comprising:
(a) at least one first detector device adapted to be held by a hand of the subject and to provide at least one respective first signal containing first data representing a respective force applied to said first detector device by at least one finger of the subject;
(b) at least one second detector device adapted to be engaged by said at least one said first detector device when held by the subject, wherein said first or said second detector device is adapted to (i) provide at least one respective second signal containing second data representing a position of said first detector device relative to a respective said second detector device and (ii) provide at least one respective third signal containing third data representing an engaging force of said first detector device on said second detector device;
(c) at least one third detector device configured to directly measure the position of part of an arm of the subject other than the hand, and adapted to provide at least one respective fourth signal containing fourth data representing a position of at least said part of said arm of the subject holding said at least one first detector device; and (d) at least one processor device for processing and comparing (i) said first data, (ii) said second data, said third data, and (iii) said fourth data, to stored values to determine potential presence of at least one neurological disorder in the subject.

2. An apparatus according to claim 1, wherein at least one said first detector device comprises at least one respective first force transducer for providing at least one respective said first signal.

3. An apparatus according to claim 1, wherein said first detector device comprises at least one second force transducer for providing at least one respective said third signal.

4. An apparatus according to claim 1, wherein at least one said second detector device has a respective engagement area having at least one position detector for providing at least one said second signal.

5. An apparatus according to claim 1, wherein at least one said third detector device comprises at least one camera.

6. An apparatus according to claim 1, further comprising at least one fourth detector device for providing at least one fifth signal containing fifth data representing an orientation of said first detector means.

7. An apparatus according to claim 1, wherein at least one said processor device is adapted to determine frequency components and/or phase of said first and/or second and/or third and/or fourth data.

8. An apparatus according to claim 1, wherein the apparatus is adapted to display a trace to be followed by the subject using said first detector device.

* * * * *